United States Patent [19]
Eidenschink et al.

[11] 4,130,502
[45] Dec. 19, 1978

[54] LIQUID CRYSTALLINE CYCLOHEXANE DERIVATIVES

[75] Inventors: Rudolf Eidenschink; Joachim Krause; Ludwig Pohl, all of Darmstadt, Germany

[73] Assignee: Merck Patent Gesellschaft mit, Darmstadt, Germany

[21] Appl. No.: 823,308

[22] Filed: Aug. 10, 1977

[30] Foreign Application Priority Data
Aug. 14, 1976 [DE] Fed. Rep. of Germany ....... 2636684

[51] Int. Cl.² ........................... C09K 3/34; G02F 1/13
[52] U.S. Cl. ..................................... 252/299; 260/463; 260/465 D; 260/465 F; 260/465 R; 350/350
[58] Field of Search ........... 260/465 R, 465 F, 465 D, 260/463; 252/299

[56] References Cited
U.S. PATENT DOCUMENTS

| | | | |
|---|---|---|---|
| 3,947,375 | 3/1976 | Gray et al. | 252/299 |
| 4,029,595 | 6/1977 | Ross et al. | 252/299 |

OTHER PUBLICATIONS
Conlonge et al., Chemical Abstracts, vol. 58, 1417e (1963).

*Primary Examiner*—Dolph H. Torrence
*Attorney, Agent, or Firm*—Millen & White

[57] ABSTRACT

Novel liquid crystals have the formula

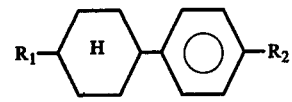

wherein one of $R_1$ and $R_2$ is cyano and the other is R, OR, OCOR or OCOOR, in which R is alkyl containing up to 12 carbon atoms.

The novel compounds can be used alone and in mixtures with each other and/or other conventional liquid crystals.

12 Claims, No Drawings

LIQUID CRYSTALLINE CYCLOHEXANE DERIVATIVES

BACKGROUND OF THE INVENTION

The present invention is concerned with liquid crystalline cyclohexane derivatives and with dielectric compositions containing them.

To an increasing extent, the properties of nematic or nematic-cholesteric liquid crystalline materials are being utilized for electro-optical indicating elements. This utility derives from the fact that the optical properties of these materials such as light scattering, birefringence, reflecting power or color, change under the influence of electric fields. The function of such indicator elements thereby depends, for example, upon the phenomenon of dynamic scattering, the deformation of aligned phases, the Schadt-Helfrich effect in the twisted cell or the cholesteric-nematic phase transition.

For the technical use of these effects in electronic elements, liquid crystalline materials which must satisfy a plurality of requirements are needed. Especially important is a chemical stability to moisture, air and physical influences, such as heat, infra-red, visible and ultra-violet radiation and direct and alternating electric fields. Furthermore, there is required a liquid crystalline mesophase in the temperature range of at least +10° C. to +60° C. and preferably of 0° C. to 60° C., and a low viscosity at ambient temperature, which should preferably be not more than 70 cP. Finally, they should not exhibit an inherent absorption of visible light, i.e., they must be colorless.

A number of liquid crystalline compounds is already known. These satisfy the stability requirements demanded of dielectrics for use in electronic display elements and are also colorless. These include, in particular, the p,p'-disubstituted benzoic acid phenyl esters described in U.S. Pat. No. 4,002,670 and the p,p'-disubstituted biphenyl derivatives described in U.S. Pat. No. 3,947,375. In both of these classes of compounds, as well as in other known series of compounds having a liquid crystalline mesophase, there are no individual compounds which form a liquid crystalline nematic mesophase in the required temperature range of 10° C. to 60° C. Therefore, as a rule, mixtures of two or more compounds are produced in order to obtain materials which can be used as liquid crystalline dielectrics. For this purpose, it is customary to mix at least two compounds, one with a low melting and clear point, the other with a distinctly higher melting and clear point. A mixture is thus normally obtained, the melting point of which is below that of the lower melting component, whereas the clear point lies between the clear points of the components. However, optimal dielectrics cannot be produced in this way since the components with the high melting and clear points almost always impart a high viscosity to the mixtures. Consequently, the switch times of the electro-optical indicator elements produced therewith are prolonged in an undesirable manner.

SUMMARY OF THE INVENTION

It is an object of the present invention to provide liquid crystalline dielectrics which exhibit a nematic phase in the required temperature range and permit short switch times in liquid crystal cells at ambient temperature.

In a composition aspect, this invention relates to novel cyclohexane derivatives of the general formula:

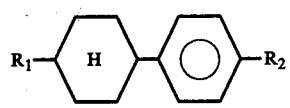

wherein one of $R_1$ and $R_2$ is cyano (CN) and the other is R, —OR, —OCOR or —OCOOR, wherein R is alkyl of up to 12 carbon atoms. In another composition aspect, this invention provides mixtures of the novel compounds of this invention. These compounds and mixtures are outstandingly useful as base materials for the production of liquid crystalline dielectrics.

Furthermore, the present invention provides liquid crystalline dielectric compositions containing at least two liquid crystalline components, at least one of which is a cyclohexane derivative of general formula (I).

This invention also provides a liquid crystal display element wherein the dielectric comprises a compound of formula (I).

DETAILED DESCRIPTION

The novel compounds of the formula (I) are, like the known p,p'-disubstituted benzoic acid phenyl esters and the p,p'-disubstituted biphenyl derivatives, colorless and possess a comparable chemical stability. The temperature range of their liquid crystalline mesophase in many cases, is surprisingly more advantageous than that of the analogously substituted previously known substances. Unexpectedly, they additionally possess a distinctly lower viscosity than the above-mentioned known base materials of liquid crystalline dielectrics.

The cyclohexane derivatives of formula (I) are 4,4'-disubstituted phenylcyclohexanes in which the radical $R_1$ and the substituted phenyl radical are present on the cyclohexane molecule in the trans-configuration. They possess a positive dielectric anisotropy of the order of +10. Therefore, they are especially suitable as components of dielectrics for indicator elements which operate on the basis of the Schadt-Helfrich effect in the twisted nematic cell or utilise the phenomenon of the cholesteric-nematic phase transition.

In the compounds of formula (I), the side groups $R_1$ and $R_2$ are different, one of the side groups being a cyano group and the other an alkyl, alkoxy, alkanoyloxy or alkoxycarbonyloxy radical. Compounds of formula (I) in which the side group $R_2$ on the aromatic ring is a cyano group are preferred because they are easier to prepare.

When $R_1$ or $R_2$ contains an alkyl radical R containing 3 or more carbon atoms, this alkyl radical can have a straight or branched chain. When $R_1$ or $R_2$ is a straight-chained alkyl radical R, compounds of formula (I) are preferred in which this alkyl radical contains 1 to 10 and preferably 3 to 8 carbon atoms. When $R_1$ or $R_2$ is a straight-chain alkoxy radical, the alkyl group therein preferably contains 1 to 8 and more preferably 1 to 6 carbon atoms. When $R_1$ or $R_2$ is a straight-chain alkanoyloxy radical (ROCO—) or a straight-chain alkoxycarbonyloxy radical (ROCOO—), the straight-chain alkyl group, R, preferably contains 1 to 6 carbon atoms. Of the compounds of formula (I) in which R is a straight-chain radical, those are preferred in which $R_1$ or $R_2$ is an alkyl or alkoxy radical.

Branched-chain alkyl radicals R in the compounds of formula (I) preferably contain not more than one chain branching. Preferred branched side groups are those in which the carbon chain is branched on the connecting carbon atom or one of the two next carbon atoms. Preferred among these are those branched radicals in which in the 1-, 2- or 3-position there is present a methyl or ethyl radical, for example, an isopropyl, 1-methylpropyl, 2-methylpropyl, 1-methylbutyl, 2-methylbutyl, 3-methylbutyl, 1-methylpentyl, 1-ethylpentyl, 2-methylpentyl, 1-methylhexyl, 2-ethylhexyl or 1-methylheptyl radical. Among these, those radicals having a main chain length of from 4 to 6 carbon atoms are preferred.

Generally, when R is a branched chain alkyl group, from 4 to 8 total carbon atoms are preferred.

Preferred side groups with a branched-chain radical R are especially those in which $R_1$ or $R_2$ is an alkoxy or alkanoyloxy radical. When such compounds contain an asymmetrically substituted carbon atom, they are optically-active and can be advantageously used as dielectrics in liquid crystalline indicator elements which operate on the basis of the cholesteric-nematic phase transition.

Contemplated classes of compounds within the scope of Formula I are those wherein:
a. $R_1$ is cyano;
b. $R_2$ is cyano;
c. $R_1$ is alkyl;
d. $R_2$ is alkyl;
e. $R_1$ is alkoxy;
f. $R_2$ is alkoxy;
g. $R_1$ is alkanoyloxy;
h. $R_2$ is alkanoyloxy;
i. $R_1$ is alkoxycarbonyloxy; and
j. $R_2$ is alkoxycarbonyloxy.

Within these, the class wherein $R_2$ is cyano and $R_1$ is a straight chain alkyl group is preferred.

The compounds of general formula (I) can be prepared in the usual manner for such compounds; for example, a compound of the general formula:

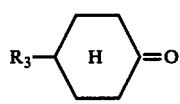

(II)

in which $R_3$ is R or OR, is reacted with phenyl lithium or with a phenyl magnesium halide, preferably phenyl magnesium bromide, followed by hydrolysis to give a compound of the general formula:

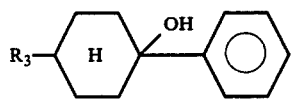

(III)

After separation of the cis-trans-isomeric alcohols (III), these are reduced in known manner to a phenylcyclohexane derivative of the general formula:

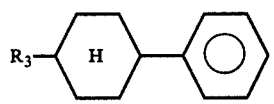

(IV)

in which $R_3$ has the same meaning as above. For example, reduction can be accomplished by catalytic hydrogenation, which proceeds with retention or inversion of the configuration of the benzyl-positioned carbon atom.

From compounds of general formula (IV) there are prepared, in known manner, the compounds of general formula (I), in which $R_2$ is a cyano group. The nitriles can be obtained by reacting a 4-($R_3$)-1-phenylcyclohexane with acetyl chloride in the presence of aluminum chloride to give a 4-[4-($R_3$)-cyclohexyl]-acetophenone which is oxidized with sodium hypochlorite to give a 4-[4-($R_3$)-cyclohexyl]-benzoic acid and this is converted into a nitrile by successive reactions with thionyl chloride, ammonia and phosphorus oxychloride via the corresponding benzoyl chloride and benzamide. Nitriles can also be obtained by reacting a 4-($R_3$)-1-phenylcyclohexane in acetonitrile with thallium tris-trifluoroacetate to give a 4-[4-($R_3$)-cyclohexyl]-phenyl thallium bis-trifluoroacetate which is then subjected to ultra-violet irradiation with potassium cyanide in aqueous solution.

For the preparation of compounds of general formula (I), in which $R_1$ is OCOR or OCOOR, 4-phenylcyclohexanol is first esterified with the corresponding acid chloride or chloroformic acid ester; subsequently, a cyano group is introduced into the phenyl nucleus in known manner, for example, as described above, by reaction with thallium tris-trifluoroacetate and ultraviolet irradiation in aqueous potassium cyanide solution.

Finally, compounds of general formula (I), in which $R_1$ is a cyano group, can be prepared by reacting cyclohexene with acetyl chloride in the presence of aluminum chloride to give 4-acetylcyclohexyl chloride which, in turn, is reacted in the presence of aluminum chloride with a compound of general formula $C_6H_5$—$R_4$, in which $R_4$ is a hydrogen atom or R, to give a 4-[4-($R_4$)-phenyl]-1-acetylcyclohexane. In this intermediate product, the acetyl radical is converted by oxidation with a hypohalogenite into a carboxyl group and this is converted conventionally via the acid chloride and acid amide, into the cyano group. From the so obtained 1-cyano-4-phenylcyclohexane ($R_4$ = H), there is subsequently prepared, for example by successive reaction with thallium tris-trifluoroacetate and lead tetraacetate, 1-cyano-4-(4-hydroxyphenyl)-cyclohexane, the hydroxyl group of which can then be converted in known manner into an RO—, ROCO— or ROCOO— radical, for example by etherification or esterification.

The starting materials for the preparation of the compounds of the present invention are either known or can be prepared without difficulty by processes known from the literature. Thus, for example, 4-alkylcyclohexanones (II, $R_3$ = R) can be obtained from the corresponding 4-alkylphenols by catalytic hydrogenation to give 4-alkylcyclohexanols which are then oxidized to ketones. Analogously, 4-alkoxycyclohexanones can be prepared by hydrogenation of the corresponding hydroquinone hemiethers and subsequent oxidation of the so obtained 4-alkoxycyclohexanols.

The compounds of formula (I) are valuable components of liquid crystalline dielectric compositions which are employed for the production of electro-optical indicator elements.

The dielectrics according to the present invention comprise two or more components, at least one of which is a compound of general formula (I). Suitable other components include preferably nematic or nematogenic substances selected from the azobenzenes, azoxybenzenes, biphenyls, Schiff bases, especially benzylidene derivatives, phenyl benzoates, optionally halogenated stilbenes, diphenylacetylene derivatives, diphenyl nitrones and substituted cinnamic acids. The most important compounds suitable as such further components can be represented by the general formula:

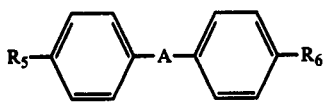
(V)

wherein A is

—CH=CH—

—CX'=CH—

—CH=CX'—

—C≡C—

—N=N—

—N(O)=N—

—N=N(O)—
—O—CO—
—CO—O—
—S—CO—
—CO—S—

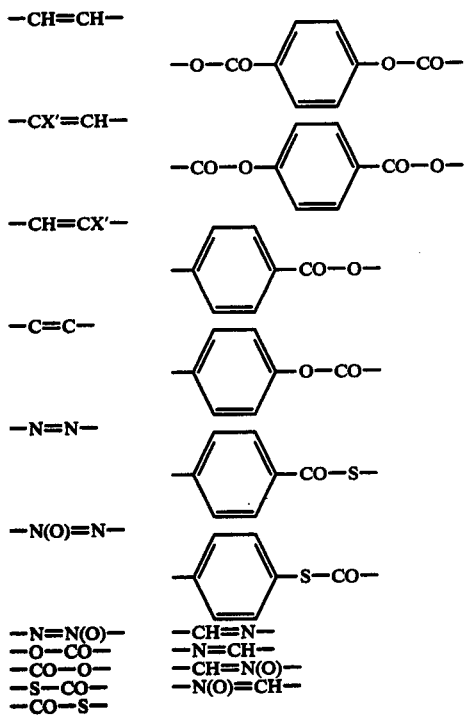

—CH=N—
—N=CH—
—CH=N(O)—
—N(O)=CH— or a carbon-carbon single bond; X' is a halogen atom and preferably a chlorine atom; and $R_5$ and $R_6$, which can be the same or different, are alkyl, alkoxy, alkanoyl, alkanoyloxy or alkoxycarbonyloxy which contain up to 18 and preferably up to 8 carbon atoms; furthermore, one of $R_5$ and $R_6$ can be cyano, nitro or isonitrile. In the case of most of these compounds, $R_5$ and $R_6$ are preferably different, one of the radicals usually being an alkyl or alkoxy radical. However, a large number of other variants of the mentioned substituents is also conventional. Many such nematic substances are commercially available.

The dielectric compositions of the present invention usually contain at least 40, preferably 50–99 and especially 60–98 parts by weight of compounds of formula (I) and optionally of formula (V). When compounds of formula (I) and of formula (V) are included, preferably at least 15 parts by weight, but usually 20 or more parts by weight, is constituted by one or more compound of formula (I). Preferably, such dielectric compositions are composed of from 20 to 99 weight parts of the compounds of formula (I) and from 80 to 1 weight parts of the compounds of formula (V). However, according to the present invention, dielectrics can also be produced which consist exclusively of two or more compounds of formula (I).

By addition of appropriate components the liquid crystalline dielectrics according to the present invention can be so modified that they can be used in all previously known kinds of liquid crystal indicator elements. Such additions are known and are described in detail in the appropriate literature. For example, there can be added substances for the alteration of the dielectric anisotropy, of the viscosity, of the conductivity and/or of the orientation of the nematic phases. Such substances are described, for example, in German Pat. Nos. 2,209,127; 2,240,864; 2,321,632; 2,338,281 and 2,450,088.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the Examples, m.p. designates melting point and c.p. the clear point of a liquid crystalline substance in degrees Celsius; boiling temperatures are indicated by b.p. If not otherwise stated, the parts or percentages are by weight.

EXAMPLE 1

(a) A solution of 280 g. of 4-n-pentylphenol in 1.5 liters of glacial acetic acid is mixed with 12 g. of platinum dioxide and hydrogenated at ambient temperature under a hydrogen pressure of 6 atm. Subsequently, the catalyst is filtered off, the solvent is distilled off and the remaining 4-n-pentyl-cyclohexanol is distilled under reduced pressure. 86.4 g. of the distillate are dissolved in 250 ml. of diethyl ether and mixed, with vigorous stirring, with a solution of 52 g. of sodium dichromate dihydrate in 25 ml. of water and 39 ml. of concentrated sulphuric acid. The reaction mixture is further stirred for 2.5 hours, whereafter the organic phase is separated off, washed twice with 200 ml. amounts of water, dried over anhydrous sodium sulphate and evaporated. The remaining 4-n-pentyl-cyclohexanone is distilled under reduced pressure; b.p. 101° C./0.1 mm. Hg.

The following compounds are prepared analogously:

4-methylcyclohexanone
4-ethylcyclohexanone
4-n-propylcyclohexanone; b.p. 49° C./0.2 mm. Hg.
4-isopropylcyclohexanone
4-n-butylcyclohexanone; b.p. 71° C./0.2 mm. Hg.
4-(1-methylpropyl)-cyclohexanone
4-(2-methylpropyl)-cyclohexanone
4-(1-methylbutyl)-cyclohexanone
4-(2-methylbutyl)-cyclohexanone
4-(3-methylbutyl)-cyclohexanone
4-n-hexylcyclohexanone; b.p. 102° C./0.4 mm. Hg.
4-(1-methylpentyl)-cyclohexanone
4-(2-methylpentyl)-cyclohexanone
4-n-heptylcyclohexanone; b.p. 110° C./0.4 mm. Hg.
4-(1-methylhexyl)-cyclohexanone
4-n-octylcyclohexanone
4-(2-ethylhexyl)-cyclohexanone
4-(1-methylheptyl)-cyclohexanone
4-n-nonylcyclohexanone
4-n-decylcyclohexanone
4-n-dodecylcyclohexanone.

(b) To a solution of phenyl magnesium bromide prepared from 80 g. of bromobenzene and 13 g. of magnesium turnings in 400 ml. of diethyl ether, there is added dropwise, with stirring and cooling, in the course of an hour, a solution of 65 g. of 4-n-pentylcyclohexanone in 200 ml. of diethyl ether. The reaction mixture is heated to boiling for a further hour and then poured into a solution of 50 ml. of concentrated hydrochloric acid in 1 liter of ice water. The ethereal phase is separated off and the aqueous phase is further shaken out twice with 100 ml. amounts of diethyl ether. The combined ethereal phases are washed neutral with 5% aqueous sodium bicarbonate solution, dried over anhydrous sodium sulphate and evaporated. The residue is subjected to a separation over a column filled with silica gel. The 1-phenyl-cis-4-n-pentyl-r-cyclohexanol eluted with petroleum ether (boiling range 40°–60° C.) is dissolved in 1 liter of ethanol and hydrogenated in the presence of 75 g. of moist Raney nickel at ambient temperature and atmospheric pressure for 72 hours. After filtering off the catalyst and distilling off the ethanol from the filtrate, the remaining trans-4-n-pentyl-1-phenylcyclohexane is distilled under reduced pressure; b.p. 105°–110° C./0.02 mm. Hg.

(c) A suspension of 16 g. of aluminum chloride in 100 ml. of dichloromethane is successively mixed, while cooling with ice, with 7.9 g. of acetyl chloride and a solution of 23 g. of 4-n-pentyl-1-phenylcyclohexane. The reaction mixture is further stirred for 2 hours, poured on to 300 g. of ice and mixed with sufficient concentrated hydrochloric acid to redissolve the precipitated aluminum hydroxide. The organic phase is separated off and the aqueous phase is washed twice with 100 ml. amounts of dichloromethane. The combined organic phases are dried over anhydrous calcium chloride and evaporated. The remaining 4-(4-n-pentyl-cyclohexyl)-acetophenone is distilled under reduced pressure; b.p. 153° C./0.02 mm. Hg.

(d) To a solution of 28 g. of sodium hydroxide and 33.6 g. of bromine in 160 ml. of water, there is added dropwise at ambient temperature, while stirring, a solution of 19 g. of 4-(4-n-pentylcyclohexyl)-acetophenone in 70 ml. of dioxane. The reaction mixture is subsequently stirred for 1 hour, mixed with a solution of 10 g. of sodium bisulphite in 100 ml. of water and adjusted to a pH value of about 5 with hydrochloric acid. 4-(4-n-Pentylcyclohexyl)-benzoic acid is isolated from the aqueous solution by two extractions with 100 ml. of amounts of dichloromethane, the extracts then being washed with water and evaporated. The 4-(4-n-pentyl-cyclohexyl)-benzoic acid thus obtained is heated to boiling for 2.5 hours with 40 ml. of thionyl chloride. After distilling off excess thionyl chloride, the remaining 4-(4-n-pentylcyclohexyl)-benzoyl chloride is dissolved in 300 ml. of anhydrous dioxane and this solution is mixed with 140 ml. of 25% aqueous ammonia solution. The reaction mixture is poured into 2 liters of ice water and the precipitated 4-(4-n-pentylcyclohexyl)-benzamide is filtered off and dried. 12.6 g. of this benzamide are dissolved at 40° C. in 200 ml. of dimethyl formamide. To this solution are added dropwise at 50° C., in the course of 30 minutes, 26 g. of phosphorus oxychloride. After 1 hour, the reaction mixture is poured into 600 ml. of ice water. By extracting four times with 200 ml. amounts of dichloromethane, washing the extracts with water, drying over anhydrous sodium sulphate and evaporating, there is obtained therefrom 4-n-pentyl-1-(4-cyanophenyl)-cyclohexane, which is purified by distillation under reduced pressure; b.p. 168° C./0.05 mm. Hg.; m.p. 30° C.; c.p. 56° C.; viscosity 21 cP at 20° C.

The following compounds are prepared analogously:

4-methyl-1-(4-cyanophenyl)-cyclohexane,
4-ethyl-1-(4-cyanophenyl)-cyclohexane,
4-n-propyl-1-(4-cyanophenyl)-cyclohexane; m.p. 42° C.; c.p. 45° C.
4-n-butyl-1-(4-cyanophenyl)-cyclohexane; m.p. 41° C.; c.p. 41° C.
4-n-hexyl-1-(4-cyanophenyl)-cyclohexane; m.p. 42° C.; c.p. 47° C.
4-n-heptyl-1-(4-cyanophenyl)-cyclohexane; m.p. 30° C. c.p. 59° C.
4-n-octyl-1-(4-cyanophenyl)-cyclohexane,
4-n-nonyl-1-(4-cyanophenyl)-cyclohexane,
4-n-decyl-1-(4-cyanophenyl)-cyclohexane,
4-n-undecyl-1-(4-cyanophenyl)-cyclohexane,
4-n-dodecyl-1-(4-cyanophenyl)-cyclohexane,
4-isopropyl-1-(4-cyanophenyl)-cyclohexane,
4-(1-methylpropyl)-1-(4-cyanophenyl)-cyclohexane,
4-(1-methylbutyl)-1-(4-cyanophenyl)-cyclohexane,
4-(2-methylbutyl)-1-(4-cyanophenyl)-cyclohexane,
4-(1-methylpentyl)-1-(4-cyanophenyl)-cyclohexane,
4-(2-methylpentyl)-1-(4-cyanophenyl)-cyclohexane,
4-(3-methylpentyl)-1-(4-cyanophenyl)-cyclohexane,
4-(2-ethylhexyl)-1-(4-cyanophenyl)-cyclohexane,
4-(1-methylheptyl)-1-(4-cyanophenyl)-cyclohexane.

EXAMPLE 2

(a) A suspension of 48 g. of silver (I) oxide and 35.2 g. of trans-4-phenylcyclohexanol in 100 ml. of n-butyl iodide is boiled for 72 hours and then filtered. After distilling off excess n-butyl iodide, the remaining 4-n-butyloxy-1-phenylcyclohexane is purified by distillation under reduced pressure.

(b) 23.2 g. of 4-n-Butyloxy-1-phenylcyclohexane and 54.3 g. of thallium tris-trifluoroacetate are boiled for 24 hours in 300 ml. of acetonitrile. Subsequently, the acetonitrile is distilled off and the remaining 4-n-butyloxy-1-[4-(bis-trifluoroacetate-thallium)-phenyl]-cyclohexane
is suspended in a solution of 80 g. of potassium cyanide in 1 liter of water. The suspension is irradiated in an immersed lamp apparatus, with vigorous stirring, for 2.5 hours with a low pressure mercury lamp. Subsequently, the reaction mixture is extracted four times with 200 ml. amounts of hexane, the extracts are dried over anhydrous sodium sulphate and evaporated and the remaining 4-n-butyloxy-1-(4-cyanophenyl)-cyclohexane is purified by distillation under reduced pressure.

The following compounds are prepared analogously:

4-methoxy-1-(4-cyanophenyl)-cyclohexane,
4-ethoxy-1-(4-cyanophenyl)-cyclohexane,
4-n-propyloxy-1-(4-cyanophenyl)-cyclohexane,
4-n-pentyloxy-1-(4-cyanophenyl)-cyclohexane,
4-n-hexyloxy-1-(4-cyanophenyl)-cyclohexane,
4-n-heptyloxy-1-(4-cyanophenyl)-cyclohexane,
4-n-octyloxy-1-(4-cyanophenyl)-cyclohexane,
4-n-nonyloxy-1-(4-cyanophenyl)-cyclohexane,
4-n-decyloxy-1-(4-cyanophenyl)-cyclohexane,
4-n-undecyloxy-1-(4-cyanophenyl)-cyclohexane,
4-n-dodecyloxy-1-(4-cyanophenyl)-cyclohexane,
4-isopropyloxy-1-(4-cyanophenyl)-cyclohexane,
4-(1-methylpropyloxy)-1-(4-cyanophenyl)-cyclohexane,
4-(1-methylbutyloxy)-1-(4-cyanophenyl)-cyclohexane,
4-(2-methylbutyloxy)-1-(4-cyanophenyl)-cyclohexane,
4-(1-methylpentyloxy)-1-(4-cyanophenyl)-cyclohexane,
4-(2-methylpentyloxy)-1-(4-cyanophenyl)-cyclohexane,
4-(3-methylpentyloxy)-1-(4-cyanophenyl)-cyclohexane, 4-(2-ethylhexyloxy)-1-(4-cyanophenyl)-cyclohexane,
4-(1-methylheptyloxy)-1-(4-cyanophenyl)-cyclohexane.

EXAMPLE 3

A solution of 35.2 g. of trans-4-phenylcyclohexanol in 200 ml. of toluene is boiled for 1 hour with 24 g. of n-pentanoyl chloride and 30 ml. of pyridine. After cooling, the reaction mixture is washed with 100 ml. of water, dried over anhydrous sodium sulphate and distilled. After stripping off the toluene and residual pyridine, there are distilled off under reduced pressure 42.7 g. of 4-n-pentanoyloxy-1-phenyl-cyclohexane. From 26 g. of this distillate there are obtained, analogously to Example 2 (b), by reaction with thallium tris-trifluoroacetate in acetonitrile and subsequent irradiation in aqueous potassium cyanide solution, 12.3 g. of 4-n-pentanoyloxy-1-(4-cyanophenyl)-cyclohexane.

The following compounds are prepared analogously:

4-acetoxy-1-(4-cyanophenyl)-cyclohexane,
4-propionyloxy-1-(4-cyanophenyl)-cyclohexane,
4-butyryloxy-1-(4-cyanophenyl)-cyclohexane,
4-hexanoyloxy-1-(4-cyanophenyl)-cyclohexane,
4-heptanoyloxy-1-(4-cyanophenyl)-cyclohexane,
4-octanoyloxy-1-(4-cyanophenyl)-cyclohexane,
4-ethoxycarbonyloxy-1-(4-cyanophenyl)-cyclohexane,
4-propyloxycarbonyloxy-1-(4-cyanophenyl)-cyclohexane,
4-butyloxycarbonyloxy-1-(4-cyanophenyl)-cyclohexane,
4-pentyloxycarbonyloxy-1-(4-cyanophenyl)-cyclohexane,
4-hexyloxycarbonyloxy-1-(4-cyanophenyl)-cyclohexane,
4-heptyloxycarbonyloxy-1-(4-cyanophenyl)-cyclohexane,
4-octyloxycarbonyloxy-1-(4-cyanophenyl)-cyclohexane,
4-nonyloxycarbonyloxy-1-(4-cyanophenyl)-cyclohexane,
4-decyloxycarbonyloxy-1-(4-cyanophenyl)-cyclohexane.

EXAMPLE 4

(a) To a suspension of 66.6 g. of anhydrous aluminum chloride in 200 ml. of carbon disulphide there are added at −15° C., with stirring, 39 g. of acetyl chloride and thereafter 41 g. of cyclohexene. The reaction mixture is stirred for 30 minutes at −15° C. and then the upper carbon disulphide layer is removed and replaced by 400 ml. of n-pentylbenzene. After the addition of a further 33 g. of aluminum chloride, while stirring, the reaction mixture is warmed up to ambient temperature and further stirred until the evolution of hydrogen chloride ceases. Thereafter, the reaction mixture is poured onto ice water, the separated aluminum hydroxide is brought into solution with hydrochloric acid and the organic phase is separated off, dried and distilled. After stripping off excess n-pentylbenzene, the 4-acetyl-1-(4-pentylphenyl)-cyclohexane thus obtained is distilled off under reduced pressure; yield 48 g.

(b) Analogously to Example 1 (d), from 27 g. of 4-acetyl-1-(4-pentylphenyl)-cyclohexane, there are obtained, by successive reaction with sodium hypobromite, thionyl chloride, ammonia solution and phosphorus oxychloride, 14.9 g. of 4-cyano-1-(4-pentylphenyl)-cyclohexane.

The following compounds are prepared analogously:

4-cyano-1-(4-methylphenyl)-cyclohexane,
4-cyano-1-(4-ethylphenyl)-cyclohexane,
4-cyano-1-(4-n-propylphenyl)-cyclohexane,
4-cyano-1-(4-n-butylphenyl)-cyclohexane,
4-cyano-1-(4-n-hexylphenyl)-cyclohexane,
4-cyano-1-(4-n-heptylphenyl)-cyclohexane,
4-cyano-1-(4-n-octylphenyl)-cyclohexane,
4-cyano-1-(4-n-nonylphenyl)-cyclohexane,
4-cyano-1-(4-n-decylphenyl)-cyclohexane,
4-cyano-1-(4-isopropylphenyl)-cyclohexane,
4-cyano-1-[4-(1-methylpropyl)-phenyl]-cyclohexane,
4-cyano-1-[4-(1-methylbutyl)-phenyl]-cyclohexane,
4-cyano-1-[4-(2-methylbutyl)-phenyl]-cyclohexane,
4-cyano-1-[4-(1-methylpentyl)-phenyl]-cyclohexane,
4-cyano-1-[4-(2-methylpentyl)-phenyl]-cyclohexane,
4-cyano-1-[4-(3-methylpentyl)-phenyl]-cyclohexane,
4-cyano-1-[4-(2-ethylhexyl)-phenyl]-cyclohexane,
4-cyano-1-[4-(1-methylheptyl)-phenyl]-cyclohexane,
4-cyano-1-(4-methoxyphenyl)-cyclohexane,
4-cyano-1-(4-ethoxyphenyl)-cyclohexane,
4-cyano-1-(4-n-propyloxyphenyl)-cyclohexane,
4-cyano-1-(4-n-butyloxypentyl)-cyclohexane,
4-cyano-1-(4-n-pentyloxyphenyl)-cyclohexane,
4-cyano-1-(4-n-hexyloxyphenyl)-cyclohexane,
4-cyano-1-(4-n-heptyloxyphenyl)-cyclohexane,
4-cyano-1-(4-n-octyloxyphenyl)-cyclohexane,
4-cyano-1-(4-n-nonyloxyphenyl)-cyclohexane,
4-cyano-1-(4-n-decyloxyphenyl)-cyclohexane,
4-cyano-1-(4-n-dodecyloxyphenyl)-cyclohexane,
4-cyano-1-(4-isopropyloxyphenyl)-cyclohexane,
4-cyano-1-[4-(1-methylpropyloxy)-phenyl]-cyclohexane,
4-cyano-1-[4-(1-methylbutyloxy)-phenyl]-cyclohexane,
4-cyano-1-[4-(2-methylbutyloxy)-phenyl]-cyclohexane,
4-cyano-1-[4-(1-methyl entyloxy)-phenyl]-cyclohexane,
4-cyano-1-[4-(2-methylpentyloxy)-phenyl]-cyclohexane,
4-cyano-1-[4-(3-methylpentyloxy)-phenyl]-cyclohexane,
4-cyano-1-[4-(2-ethylhexyloxy)-phenyl]-cyclohexane,
4-cyano-1-[4-(1-methylheptyloxy)-phenyl]-cyclohexane.

The following Examples describe liquid crystalline dielectric compositions according to the present invention:

EXAMPLE 5

A mixture of 40 parts by weight of 4-n-pentyl-1-(4-cyanophenyl)-cyclohexane,
25 parts by weight of 4-n-heptyl-1-(4-cyanophenyl)-cycohexane, and
35 parts by weight of 4-n-butyloxy-1-(4-cyanophenyl)-cyclohexane has a positive dielectric anisotropy of $\Delta \epsilon \sim 10$. The dielectric, in a twisted nematic cell with 10 micrometers plate distance is light permeable between crossed polarizers. Upon applying a voltage of 1.5 V, the area between the electrodes is dark.

EXAMPLE 6

A mixture of 37.5 parts by weight of 4-n-pentyl-1-(4-cyanophenyl)-cyclohexane,
25 parts by weight of 4-n-heptyl-1-(4-cyanophenyl)-cyclohexane,
34 parts by weight of 4-n-butyloxy-1-(4-cyanophenyl)-cyclohexane,
3 parts by weight of cholesterol pelargonate and
0.5 parts by weight of 4-N,N-diethylaminophenylazo-(5-nitro)-thiazole is, as the dielectric in a liquid crystal cell with 15 micrometers plate distance, planar-cholesteric oriented and exhibits a deep blue color. When to oppositely-lying transparent electrodes of this cell there is applied an alternating voltage of 20V/50Hz, the areas of the dielectric present between these electrodes are transparent.

EXAMPLE 7

A mixture of 29 parts by weight of 4-n-propyl-1-(4-cyanophenyl)-cyclohexane,
41 parts by weight of 4-n-pentyl-1-(4-cyanophenyl)-cyclohexane and
30 parts by weight of 4-n-heptyl-1-(4-cyanophenyl)-cyclohexane has a nematic phase in the temperature range of from −5° C. to +51° C., a dielectric anisotropy of +10.1 and a viscosity of 21 cP at 20° C.

EXAMPLE 8

. A mixture of 30 parts by weight of 4-n-octyloxy-4'-cyanobiphenyl,
21 parts by weight of 4-n-propyl-1-(4-cyanophenyl)-cyclohexane,
28 parts by weight of 4-n-pentyl-1-(4-cyanophenyl)-cyclohexane and
21 parts by weight of 4-n-heptyl-1-(4-cyanophenyl)-cyclohexane has a nematic phase in the temperature range of from −7° C. to +56° C., a dielectric anisotropy of +11.3 and a viscosity of 29 cP at 20° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modification of the invention to adapt it to various usages and conditions.

What is claimed is:

1. Compounds of the formula:

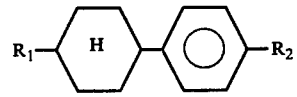

wherein $R_2$ is cyano and $R_1$ is R, OR, OCOR or OCOOR, in which R is alkyl of up to 12 carbon atoms.

2. A compound of claim 1, wherein R is straight-chained.

3. A compound of claim 1, wherein R is a branched alkyl radical with only one chain branching.

4. A compound of claim 1, wherein $R_1$ is R or OR.

5. The compound of claim 1 which is 4-n-pentyl-1-(4-cyanophenyl)-cyclohexane.

6. The compound of claim 1 which is 4-n-propyl-1-(4-cyanophenyl)-cyclohexane.

7. The compound of claim 1 which is 4-n-butyl-1-(4-cyanophenyl)-cyclohexane.

8. The compound of claim 1 which is 4-n-hexyl-1-(4-cyanophenyl)-cyclohexane.

9. The compound of claim 1 which is 4-n-heptyl-1-(4-cyanophenyl)-cyclohexane.

10. The compound of claim 1 which is 4-n-butyloxy-1-(4-cyanophenyl)-cyclohexane.

11. The compound of claim 1 which is 4-n-pentanoyloxy-1-(4-cyanophenyl)-cyclohexane.

12. A mixed liquid crystalline dielectric composition containing at least 40% of a compound of claim 1.

UNITED STATES PATENT AND TRADEMARK OFFICE
CERTIFICATE OF CORRECTION

PATENT NO. : 4,130,502
DATED : December 19, 1978
INVENTOR(S) : Rudolf Eidenschink et al It is certified that error appears in the above-identified patent and that said Letters Patent are hereby corrected as shown below:

Assignee: reads " Merck Patent Gesellschaft mit, Darmstadt, Germany"

should read -- Merck Patent Gesellschaft Mit Beschränkter Haftung, Darmstadt, Germany --

Signed and Sealed this

Eighth Day of May 1979

[SEAL]

Attest:

RUTH C. MASON
Attesting Officer

DONALD W. BANNER
Commissioner of Patents and Trademarks